United States Patent
Stucker

(10) Patent No.: US 12,171,248 B2
(45) Date of Patent: Dec. 24, 2024

(54) METHOD FOR INCREASING RATE AND EXTENT OF FIBER DIGESTION IN RUMINANTS

(71) Applicant: Dennis R. Stucker, Clay, NY (US)

(72) Inventor: Dennis R. Stucker, Clay, NY (US)

(73) Assignee: IMPETUS LLC, Clay, NY (US)

( * ) Notice: Subject to any disclaimer, the term of this patent is extended or adjusted under 35 U.S.C. 154(b) by 642 days.

(21) Appl. No.: 17/295,574

(22) PCT Filed: Nov. 21, 2019

(86) PCT No.: PCT/US2019/062559
§ 371 (c)(1),
(2) Date: May 20, 2021

(87) PCT Pub. No.: WO2020/106929
PCT Pub. Date: May 28, 2020

(65) Prior Publication Data
US 2023/0180790 A1 Jun. 15, 2023

Related U.S. Application Data

(60) Provisional application No. 62/770,312, filed on Nov. 21, 2018.

(51) Int. Cl.
*A23K 10/14* (2016.01)
*A23K 10/30* (2016.01)
(Continued)

(52) U.S. Cl.
CPC .............. *A23K 10/14* (2016.05); *A23K 10/30* (2016.05); *A23K 20/189* (2016.05); *A23K 20/24* (2016.05); *A23K 50/10* (2016.05)

(58) Field of Classification Search
CPC ...... A23K 10/14; A23K 10/30; A23K 20/189; A23K 20/22; A23K 20/24; A23K 40/10; A23K 50/10
(Continued)

(56) References Cited

U.S. PATENT DOCUMENTS 4,225,620 A * 9/1980 Rawlings ............... A23K 10/24
426/647
5,118,397 A * 6/1992 Sweeney ............... A23K 10/32
426/236
(Continued)

FOREIGN PATENT DOCUMENTS

CN 107509853 A * 12/2017
WO WO-9957993 A1 * 11/1999 ............. A23K 10/14
(Continued)

OTHER PUBLICATIONS

Carr et al.; "Corn Silage Preservation with Anhydrous Ammonia, Live Culture Microbial, or Organic Acid-Based Additives"; Journal of Dairy Science vol. 67, No. 7, 1984; https://www.journalofdairyscience.org/article/S0022-0302(84)81464-2/pdf (Year: 1984).*
(Continued)

*Primary Examiner* — Drew E Becker
*Assistant Examiner* — Austin Parker Taylor
(74) *Attorney, Agent, or Firm* — Barclay Damon LLP

(57) ABSTRACT

A method for treating a forage to increase digestibility by a ruminant comprises providing a forage for a ruminant comprising a level of ammonia that is from 0.0% to about 1.4% of dry matter (wt/wt). An alkali is applied at a dosage of from about 0.25% to about 0.75% of dry matter (wt/wt) to the forage. At least one exogenous carbohydrase enzyme is applied to the forage after application of the alkali and the forage is subsequently fed to the ruminant.

19 Claims, 2 Drawing Sheets

(51) Int. Cl.
  *A23K 20/189* (2016.01)
  *A23K 20/24* (2016.01)
  *A23K 50/10* (2016.01)
(58) Field of Classification Search
  USPC .................................. 426/49, 52, 53, 54
  See application file for complete search history.

(56) References Cited

U.S. PATENT DOCUMENTS

| | | | | |
|---|---|---|---|---|
| 5,922,343 | A * | 7/1999 | Stucker | A23K 10/14 |
| | | | | 424/94.2 |
| 2009/0263538 | A1* | 10/2009 | Harris | A23K 20/147 |
| | | | | 426/2 |
| 2010/0136176 | A1 | 6/2010 | Miller et al. | |
| 2011/0081442 | A1* | 4/2011 | Weill | G01N 33/06 |
| | | | | 73/866 |
| 2011/0200705 | A1* | 8/2011 | Tricarico | A23K 50/10 |
| | | | | 426/2 |
| 2015/0118349 | A1 | 4/2015 | Cecava et al. | |
| 2016/0324190 | A1* | 11/2016 | Delord | C12Y 302/01004 |

FOREIGN PATENT DOCUMENTS

| | | | | |
|---|---|---|---|---|
| WO | WO-0237981 | A2 * | 5/2002 | A23K 10/30 |
| WO | 2009/006362 | A1 | 1/2009 | |

OTHER PUBLICATIONS

Bagley, Clell V.; "Toxic Contaminants in Harvested Forages"; Utah State University Extension; Jul. 1997; https://digitalcommons.usu.edu/cgi/viewcontent.cgi?article=1093&context=extension_histall (Year: 1997).*
K.M. Young et al.; Effect of Exogenous Protease Enzymes on the Fermentation and Nutritive Value of Corn Silage; Journal of Dairy Science 95:6687-6694; Apr. 16, 2012.
E. Raffrenato et al,; Technical note: Improved Methodology for Analyses of Acid Detergent Fiber and Acid Detergent Lignin; Journal of Dairy Science 94:3613-3617; Aug. 9, 2010.
E. Raffrenato et al,; Development of an in Vitro Method to Determine Rumen Undigested aNDForm for Use in Feed Evaluation; Journal of Dairy Science 101:9888-1501; May 22, 2018.
C.E. Polan et al.; Urea-Treated Corn Silage as the Only Forage for Lactating Cows; Journal of Dairy Science, vol. 51, No. 9; Mar. 11, 1968.
M. Oba et al.; Evaluation of the Importance of the Digestibility of Neutral Detergent Fiber From Forage: Effects on Dry Matter Intake and Milk Yield of Dairy Cows; Journal of Dairy Science 82:589-596; May 4, 1998.
S.J. Meale et al.; Board-Invited Review: Opportunities and Challenges in Using Exogenous Enzymes to Improve Ruminant Production; Journal of Animal Science 2014.92.427-442; Nov. 24, 2014.
J. Lopez et al.; Redistribution of Nitrogen in Urea-Treated and Soybean Meal-Treated Corn Silage; Journal of Dairy Science, vol. 53, No. 9; Jan. 26, 1970.
L. Kung Jr., et al.; The Effect of an Exogenous Protease On the Fermentation and Nutritive Value of High-Moisture Corn; Journal of Dairy Science 97:1707-1712; Sep. 9, 2013.
L. Kung et al.; Interpretation and Use of Silage Fermentation Analysis Reports; Focus on Forage, vol. 3, No. 13; on or before Dec. 31, 2001.
J.T. Huber et al.; Ammonia-Treated Corn Silage for Dairy Cattle; Journal of Dairy Science, vol. 55, No. 4; Sep. 22, 1971.
H.K. Goering et al.; Forage Fiber Analyses; US Department of Agriculture, Agriculture Handbook No. 379, Jacket No. 387-598; on or before Dec. 31, 1970.
L.F. Ferraretto et al.; Relationships Between Dry Matter Content, Ensiling, Ammonia-Nitrogen, and Ruminal in Vitro Starch Digestibility in High-Moisture Corn Samples; Journal of Dairy Science 97:3221-3227; Nov. 4, 2013.
L.F. Ferraretto et al.; Influence of Ensiling, Exogenous Protease Addition, and Bacterial Inoculation On Fermentation Profile, Nitrogen Fractions, and Ruminal in Vitro Starch Digestibility in Rehydrated and High-Moisture Corn; Journal of Dairy Science 98:7318-7327; Jun. 1, 2015.
DeHaan; Improving the Utilization of Fiber and Energy Through the Use of Corn Gluten Feed and Alkali Compounds; on or before May 30, 1983.
Bals et al.; Ammonia Fiber Expansion (AFEX) Treatment of Eleven Different Forages: Improvements to Fiber Digestibility In Vitro; Animal Feed Science and Technology 155 (2010) 147-155; Apr. 7, 2009.
Dahlke; An On-Farm Demonstration of Calcium Hydroxide Treatment of Corn Silage With Subsequent Observations in the Cooperating Dairy Herd; Iowa State University Animal Industry Report 2014; AS 660, ASL R2839; on or before Dec. 31, 2014.
Cotanch et al.; Applications of Undf in Ration Modeling and Formulation; Cornell University; Oct. 21, 2014.
Cotanch; Using 240 Hour uNDF in the Field; Cornell University; Oct. 19, 2015.
Cook et al; The Effects on Digestibility and Ruminal Measures of Chemically Treated Corn Stover as a Partial Replacement for Grain in Dairy Diets; Journal of Dairy Science 99:6342-6351; Sep. 15, 2015.
Carr et al.; Corn Silage Preservation and Anhydrous Ammonia, Liver Culture Microbial, or Organic Acid-Based Additives; Journal of Dairy Science 67:1474-1481; Mar. 28, 2983.
Beauchemin et al; Enzymes in Farm Animal Nutrition, $2^{nd}$ Edition; Chapter 8: Developments in Enzyme Usage in Ruminants; CAB International; on or before Nov. 30, 2010.
Beauchemin et al; Use of Exogenous Fibro Lytic Enzymes to Improve Feed Utilization by Ruminants; Journal of Animal Science 81(E. Suppl. 2):E37-47; Jun. 6, 2002.
Adesogan; Improving Forage Quality and Animal Performance With Fibro Lytic Enzymes; 2005 Florida Ruminant Nutrition Symposium; on or before Dec. 31, 2005.
Van Soest; The Detergent System for Analysis of Foods and Feeds; ISBN: 978-1-63095-134-4; on or before Dec. 31, 2015.
PCT/US2019/062559, filed Nov. 21, 2019. International Preliminary Report on Patentability (6 pages).

* cited by examiner

METHOD FOR INCREASING RATE AND EXTENT OF FIBER DIGESTION IN RUMINANTS

CROSS REFERENCE TO RELATED APPLICATIONS

This application is a national stage application pursuant to 35 U.S.C. § 371 of International Application No. PCT/US2019/062559, filed on Nov. 21, 2019, which claims the benefit of and priority to U.S. Provisional Patent Application Ser. No. 62/770,312, filed Nov. 21, 2018 and entitled "METHOD FOR INCREASING RATE AND EXTENT OF FIBER DIGESTION IN RUMINANTS." The entire contents of said applications are incorporated herein by reference.

TECHNICAL FIELD

The present invention relates to methods for increasing rates and extent of fiber digestion in ruminants, and specifically to methods for treating ruminant forage to increase its digestibility by ruminants.

BACKGROUND

Selected exogenous enzymes are currently used as feed additives for monogastric species, specifically swine and poultry. Exogenous enzymes applied to feed are used, for example to supplement the endogenous digestive enzymes in the host animal, to remove anti-nutritional factors such as beta-glucans from problem feedstuffs such as barley, to render certain nutrients readily available such as phosphorus, and to enhance the energy value of feed stuffs.

Owing to the characteristics of the digestive system in ruminant animals (also referred to herein as "ruminants"), a ruminant's diet, unlike a monogastric diet, includes a significant portion of forages that contain high levels of plant structural carbohydrates, commonly quantified and referred to as fiber, and more specifically neutral detergent fiber (NDF). A positive correlation exists between NDF digestibility (NDFd), dry matter intake, and milk yield in dairy cattle, resulting in improved profitability of milk production. Conversely, the fiber that is undigested in ruminants (uNDF) limits dry matter intake, milk yield, and profitability. Additionally, there is a negative correlation between NDFd and enteric methane emissions. As NDFd increases, enteric methane produced per unit of feed consumed, or per unit of milk produced, decreases. Conversely, as NDFd decreases, enteric methane produced per unit of feed consumed, or per unit of milk produced, increases.

U.S. Pat. No. 5,922,343 entitled "Method of Introducing Carbohydrase Enzymes to a Ruminant Feed for Increasing the Rate and Extent of Fiber Digestion in the Ruminant" to Stucker and United States Patent Application No. US2004102026697A1 entitled "Use of Proteolytic Enzymes to Increase Feed Utilization in Ruminant Diets" by Beauchemin et al., both disclose methods for increasing neutral detergent fiber digestibility (NDFd). U.S. Pat. No. 5,922,343 discloses a method for increasing NDFd comprising applying a dilute aqueous solution of exogenous carbohydrase enzymes (ECE) directly to ruminant forage immediately prior to feeding. In addition, US2004/0202697A1 discloses a method for increasing NDFd comprising introducing a protease enzyme to an animal's diet by either applying the protease to the forage or by incorporating the protease into other components of the animal's diet as a feed additive.

Neither of the methods disclosed in U.S. Pat. No. 5,922,343 and in US2004/0202697A1 has been widely adopted owing to lack of measurable and/or consistent commercial animal responses.

In the United States, about 7 million acres of the U.S. corn crop is harvested annually as corn silage, yielding about 113 million tons of silage. This is the predominant forage in most U.S. dairy rations. There is an interaction between NDFd and the ambient temperature during different stages of plant growth and between the amount of rain fall during different stages of plant growth. Since the corn silage NDFd is determined largely by uncontrollable weather and agronomic factors, any management technique or technology that improves corn silage NDFd will improve dairy productivity.

Recent research into current methods for utilizing ECE for improvement of NDFd in ruminant rations shows that results from individual studies are too variable, inconsistent, and unpredictable for widespread commercial adoption. The inconsistent efficacy of these methods may be attributed, at least in part, to variations in activity of various enzymes and enzyme combinations used in the various experiments, and to variation in the methods of application of the enzymes to forage. For example, in some methods, enzymes were introduced into the grain/concentrate portion of the total ration (feed ration) and then the grain/concentrate portion of the total ration was subsequently mixed with the forage portion of the ration. In yet other methods, enzymes were applied directly to the forage portion of the total ration. Interactions also varied between enzymes and various types of forage or tertiary plant compounds (e.g., tannins, cutins, and esterified linkages).

As an alternative to using enzymatic treatments to increase NDFd, alkali treatments such as calcium hydroxide (CaOH) have been investigated as a treatment method to increase NDFd in corn silage. Alkali in the form of calcium hydroxide added at 5% by weight of forage dry matter has been shown to increase NDFd when allowed adequate time for the alkali to penetrate through forage particle surface area and hydrolyze lignin bonds. In one trial, calcium hydroxide was added to corn silage at a dosage of 5% by weight of dry matter (e.g., 50 lbs. of dry CaOH per 1000 lbs. of corn silage) at the time of harvest and ensiling. The corn silage was allowed to ferment for 60 days. The treated corn silage had a statistically significant higher NDFd. However, applying calcium hydroxide to corn silage at harvest required additional equipment, slowed the harvesting process, and resulted in less aerobically stable silage. These drawbacks make this treatment methodology undesirable for commercial applications.

In one study, treatment of corn silage with calcium hydroxide decreased NDFd (NDF digestibility after 30 hours of exposure to rumen fluid in-vitro) from time of ensiling to eight months post ensiling. In another study, calcium hydroxide treatment showed no improvement in animal performance (i.e., weight gain of animal) when added to a total mixed ration for beef steers. In other studies, calcium hydroxide was added at a dosage 5% per dry weight of corn stalks. This dosage increased NDFd, but the treatment dosage must be added at 5% per dry weight of corn stalks plus added water to attain 50% moisture, which then must ensiled for a minimum of 30-60 days. Furthermore, the application of an alkali to forages at a dosage rate equal to 5% wt/wt of dry matter results in a significant exothermic reactions thereby elevating the temperatures of the forage. Accordingly, the forage must be allowed to cool back down to ambient temperature prior to feeding. Failure to do so will result in decreased feed intakes and subsequent reductions in milk yield. Another known treatment, ammonia fiber expansion (AFEX) treatment, requires an interaction between an aqueous ammonia solution and the crop residue biomass under elevated temperatures and pressures. This treatment has been shown to increase the fiber digestibility of low digestible crops such as switch grass and corn stover, but shows no improvement in digestibility of corn silage fiber.

Research has further shown that elevated levels of ammonia ($NH_3$) is not a desirable fermentation characteristic in that it is indicative of low dry matter recovery. The dry matter recovery refers to the amount of dry matter removed from storage versus the amount of dry matter placed into storage. Silages are harvested at approximately 35% dry matter (65% moisture) and compressed to remove oxygen. The silage then undergoes an acidic fermentation by naturally occurring bacteria present on the crop. A properly harvested and stored silage will have a high amount of dry matter recovery (95% or more) and a poorly harvested and stored silage will have a low amount of dry matter recovery (80% or less).

Corn silages with high ammonia generally have poor fermentations and extended aerobic fermentation because the lactic acid production was low and pH remained well above 4.0. Corn silages with elevated ammonia levels are relatively rare: less than 5% of the 5,787 corn silage samples analyzed from 2014 thru 2018 by Cumberland Valley Analytical Services had ammonia levels greater than 1.4% (crude protein equivalent/% dry matter) of dry matter (personal communication from Cumberland Valley Analytical Services, Waynesboro, PA to inventor, August 2018).

Ammonia level of ensiled high moisture corn has been shown to increase as length of fermentation time increases due to continual degradation of protein under acidic anaerobic conditions. For example, adding exogenous proteases to high moisture corn increases ammonia concentrations above non-treated controls. This has been shown to be the result of hydrolysis of zein by native plant proteases and/or exogenous proteases. Higher ammonia content has been shown to correlate to higher 7-hour in-vitro starch digestion, but has not been shown to affect NDFd. Applying exogenous protease to whole plant corn silage at harvest has shown effects similar to applying exogenous protease to high moisture corn at harvest, bringing about increased ammonia, increased starch digestibility, and no change in NDFd.

An alternative approach that yields high ammonia levels in corn silage is adding non-protein nitrogen (NPN) in the form of anhydrous ammonia, aqueous ammonia, or urea at time of ensiling. These studies have shown the addition of NPN in any of these forms increased ammonia content of the fermented corn silage. When the NPN that is added at time of ensiling is urea, it was converted to ammonia during the course of the ensiling process. The amount of conversion of urea to ammonia increased over the length of ensiling time. The addition of the NPN in any form did not increase fiber digestibility either as measured directly or as indicated by changes in dry matter intake.

Definitions

Ruminant(s)—A mammal(s) that is able to acquire nutrients from plant-based food by fermenting it in a specialized stomach prior to digestion. The process typically requires the fermented ingesta or cud to be regurgitated and chewed again. Examples of a ruminant for which the disclosed methods apply include, but are not limited to, cattle, goats, sheep, giraffes, yaks, deer, and antelope.

Forage—A plant material eaten by ruminants. Examples of forage include, but are not limited to, corn silage, sorghum silage, wheat silage, oat silage, grass silage, or alfalfa silage.

Feed/Feed Ration—A mixture of forage(s), grain, protein concentrates, and minerals.

Neutral Detergent Fiber (NDF)—The insoluble fibrous plant parts that remain following neutral detergent digestion where a neutral detergent dissolves plant pectins, proteins, sugars, and lipids.

Neutral Detergent Fiber Digestibility (NDFd)—The level of neutral detergent fiber digestibility after thirty (30) hours of exposure to rumen fluid in-vitro.

Exogenous carbohydrase enzyme (ECE)—An enzyme added to an animal's feed that enhances the animal's natural digestion of carbohydrates.

Alkali—A basic, ionic salt of an alkali metal or chemical element that can be dissolved in water to produce an aqueous solution with a pH greater than 7.

Dry Matter—Forage material or material comprising no (0%) moisture. For example, a silage comprising 35% dry matter would contain 65% moisture (water).

SUMMARY

An embodiment of a method for increasing fiber digestion of a forage by a ruminant comprises providing a forage for a ruminant, wherein the forage comprises an ammonia level of 0.0-1.4% of dry matter (crude protein equivalent/% dry matter). An alkali is applied to the forage at a dosage of 0.25%-0.75% of dry matter (wt/wt) while mixing the forage. At least one exogenous carbohydrase enzyme is applied to the forage while the forage is being mixed. The at least one exogenous carbohydrase enzyme comprises at least 70% active carbohydrase enzyme. The forage is then fed to the ruminant.

Another embodiment of the method for treating a forage to increase digestibility by a ruminant comprises providing a forage for a ruminant comprising a level of ammonia that is not more than 1.4% of dry matter (crude protein equivalent/% dry matter). An alkali is applied to the forage at a dosage of 0.25%-0.75% of dry matter (wt/wt). At least one exogenous carbohydrase enzyme is applied to the forage after application of the alkali and the forage is subsequently fed to the ruminant.

Additional features and advantages of the present disclosure are described in, and will be apparent from, the following Brief Description of the Drawings and Detailed Description.

DETAILED DESCRIPTION OF THE INVENTION

The following discussion relates to various embodiments of a method for increasing the rate and the extent of fiber digestion in ruminants. It will be understood that the herein described versions of the method are examples that embody certain inventive concepts as detailed herein. To that end, other variations and modifications will be readily apparent to those of sufficient skill. In addition, certain terms are used throughout this discussion in order to provide a suitable frame of reference and are not intended to limit these concepts, except where so specifically indicated. For example, the term "about" or "approximately" is meant to encompass a range of 80-120% of the disclosed value.

Figure 1:
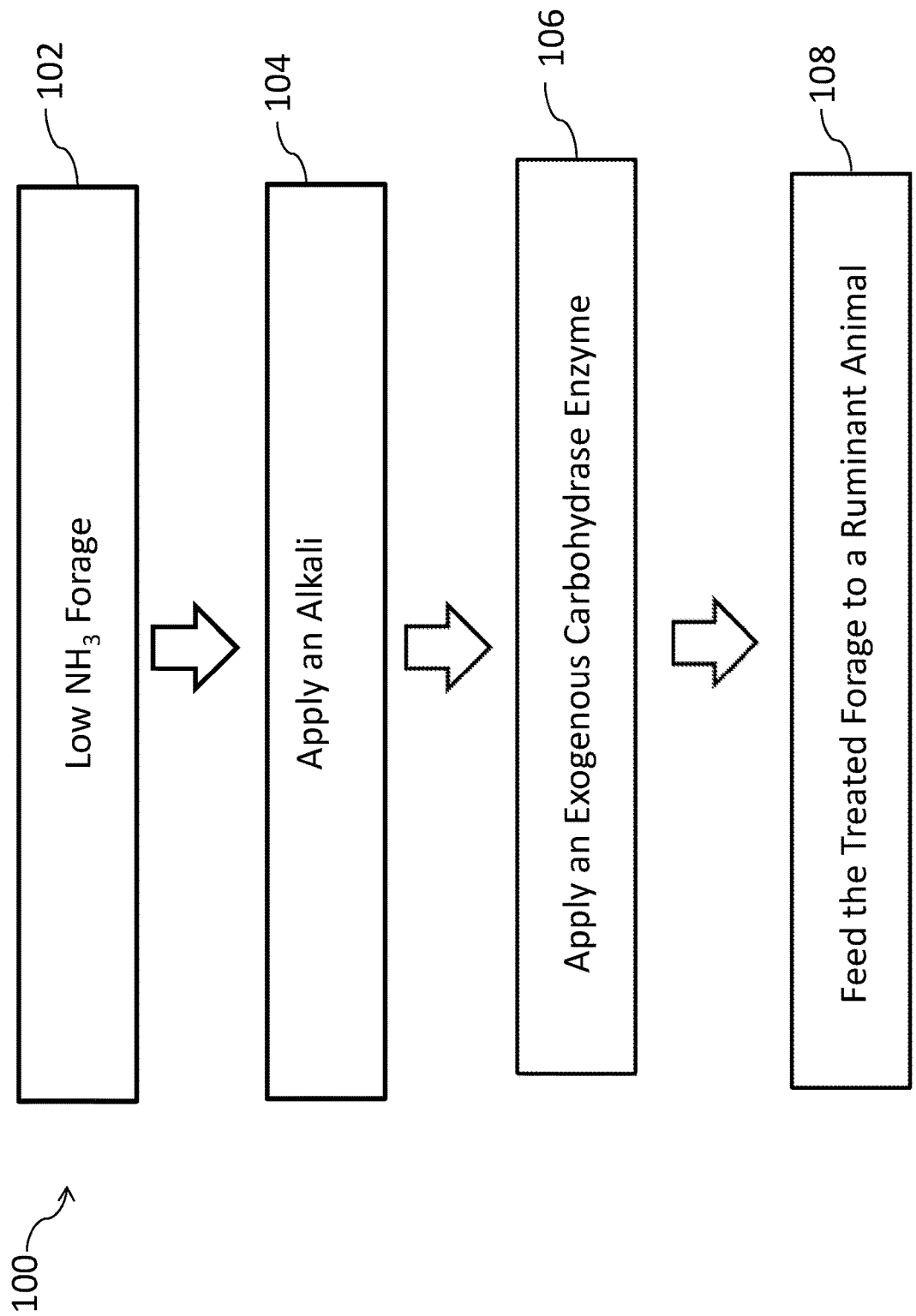
FIG. 1 illustrates a schematic depiction of an embodiment of a method for increasing rate and extent of fiber digestion in ruminants.

A method for treating ruminant forage having a low level of ammonia is disclosed herein. The method further increases rate and extent of fiber digestion by a ruminant of a forage having a low level of ammonia. Referring to FIG. 1, in an embodiment, the method 100 generally starts with providing a forage with a low level of ammonia 102. The level of ammonia contained in the forage may be determined by any known methods/procedures. The forage having a low level of ammonia is then treated prior to feeding to the ruminant. The first step 104 in the treatment is applying an alkali to the forage. An exogenous carbohydrase enzyme or plurality of exogenous carbohydrase enzymes (referred to herein as "ECE") is then applied to the alkali treated forage 106 in order to complete the treatment. The treated forage is then fed to a ruminant 108. Feeding a ruminant a forage treated in the above manner yields a consistent, predictable, and efficacious improvement in the neutral detergent fiber digestibility (NDFd) in the ruminant and a decrease in the variability in ruminant response to the treated forage.

Figure 2:
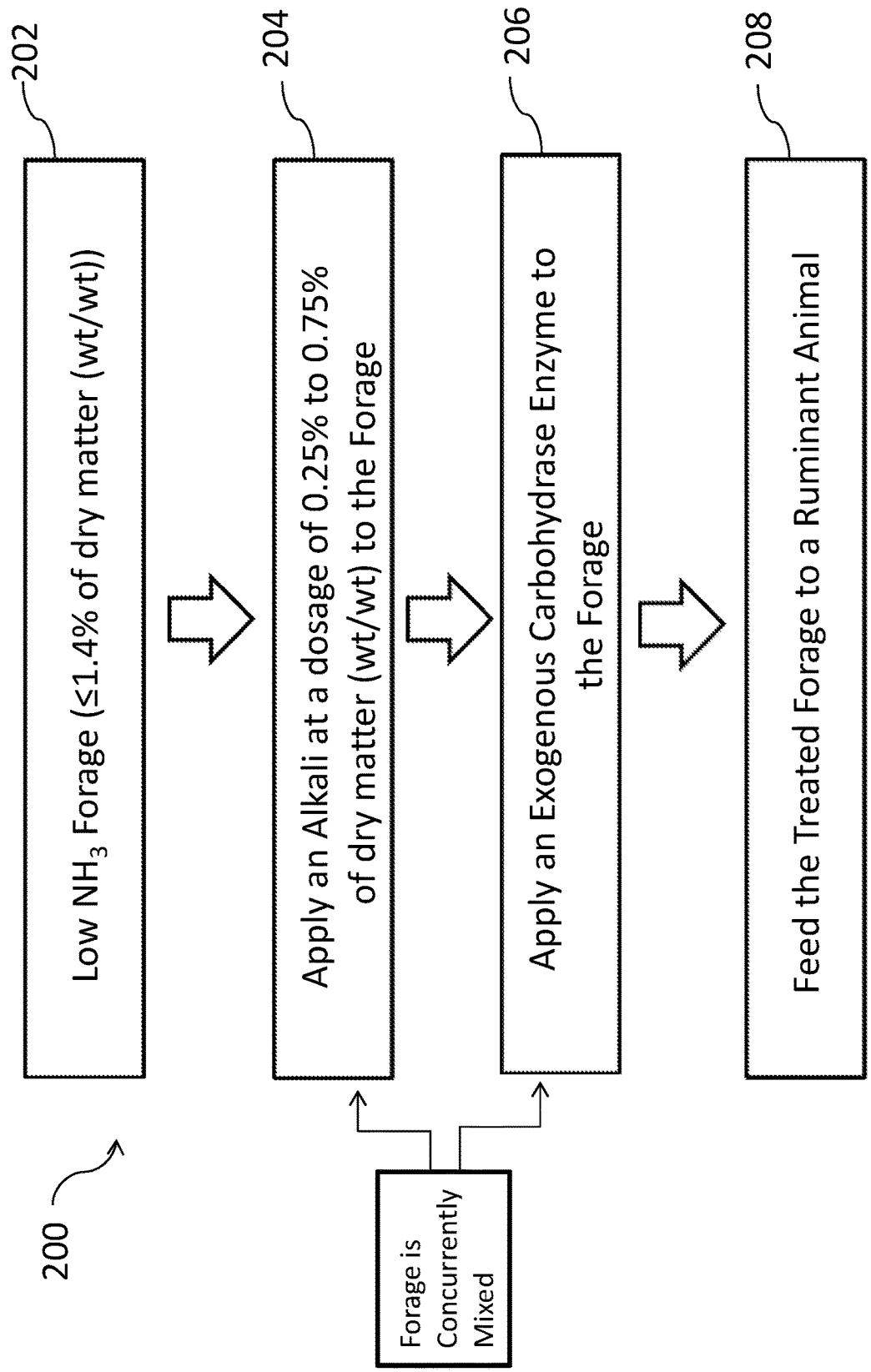
FIG. 2 illustrates a schematic depiction of another embodiment of the method for increasing rate and extent of fiber digestion in ruminants.

Referring to FIG. 2, in an embodiment, a low level of ammonia (NH3) in the forage is defined as being no higher than 1.4% of dry matter (crude protein equivalent/% dry matter) or from 0.0-1.4% of dry matter (crude protein equivalent/% dry matter) 202. In an embodiment, the method 200 comprises applying an alkali to the forage at a dosage of 0.25% to 0.75% of dry matter (wt/wt) 204. After application of the alkali, an ECE is applied to the forage 206. After the ECE is applied, the treatment is complete. As shown in the embodiment illustrated in FIG. 2, the application of the alkali and the ECE was done while the forage was concurrently mixed 210. The forage is then fed to the ruminant 208 0-5 minutes after treatment of the forage is completed. In other embodiment, the forage is fed to the ruminant more than five (5) minutes after the treatment is completed. In an embodiment, the forage is rested for a period of time greater than five (5) minutes before it is fed to the ruminant. The treated forage can be introduced to the ruminant prior to substantial activity by the ECE on the forage. In another embodiment, the ECE is applied to the forage at least three (3) minutes prior to ingestion by the ruminant. The disclosed methods do not require compaction or cubing the forage or ration of feed before ingestion by the ruminant. The process of cubing requires exposing the forage or ration of feed to high humidity, elevated temperatures and pressure which may initiate and cause substantial fiber degradation by the enzymes prior to ingestion by the ruminant. Moreover, the increased temperature and pressure of the cubing process may degrade or otherwise denature the ECE.

In certain commercial settings, a ruminant's total feed ration, typically grain and protein concentrates, minerals, and forages, is mixed (e.g., in a feed mixer) and delivered to the ruminant once or twice per day. According to the present methods, if the forage contained in the feed has a low ammonia content, then an alkali pre-treatment is applied. The ECE is next applied, which increases NDFd, and then the total ration is immediately delivered to the ruminant animal. In an embodiment, application of the alkali and/or the ECE comprises evenly distributing the alkali and/or the ECE across the surface area of each particle of the forage. Such an application may involve spraying, turning, or otherwise mixing the forage to ensure even distribution of treatment applications.

Exogenous Carbohydrase Enzyme(s) (ECE)

An aqueous ECE solution may be comprised of diluting an ECE concentrate. The ECE concentrate can be used that comprises at least 70% active carbohydrase enzymes. In an embodiment, the ECE concentrate comprises 90% active carbohydrase enzymes and 10% carrier(s), such as glucose and glycerol. An example of a suitable commercially available ECE comprises three major classes of enzymes: Cellulase 11,500 ECU/ml (ECU=endo-cellulase unit); Xylanase 28,750 BXU/ml (BXU=beta-xylanase unit); Polygalacturonase 45.5 PGU/ml (PGU=endo-polygalacturonase unit).

In an embodiment, the ECE is applied to the forage at a rate of approximately 0.25 ml to 2.50 ml of ECE concentrate per pound of forage dry matter (ml/wt). In other embodiments, 1-10, 10-20, 20-30 30-40 40-50 or 50-60 ml of ECE concentrate comprises about 70-90% active carbohydrase enzyme is added to 400-16,000 ml of water to form an aqueous ECE solution. In an embodiment, a dose for an individual ruminant is 3-30 ml of ECE concentrate that comprises about 70-90% active carbohydrase enzyme is added to 3,500-4,500 ml of water to form an aqueous ECE solution. This dose of ECE is given on a per head per day basis, assuming an intake of 24 lb. of forage dry matter per day. In other embodiments, the ratio of ECE concentrate to water is 1 ml (±0.5 ml) ECE concentrate to 20-400 ml of water. In other embodiments, 0.75-10 ml, 10-20 ml, 20-100 ml, 100-200 ml, 200-300 ml, 300-400 ml or 400-500 ml of ECE concentrate is diluted water to make 2,000-10,000 ml (2-10 liters) of aqueous ECE solution. In an embodiment, 18 ml of the ECE concentrate is added to 3,982 ml of water to form a 4,000 ml aqueous ECE solution. This aqueous ECE solution is applied at a dosage of 160 ml of the aqueous ECE solution per pound of forage dry matter.

Generally, once the ECE is applied to the forage it begins to breakdown or hydrolyze the polysaccharides present in the forage to monosaccharides (simple sugars). These polysaccharides include structural carbohydrates like cellulose. The longer the ECE is left on the forage prior to ingestion, the more opportunity the ECE has to work on the forage or the more activity the ECE has on the forage prior to the forage entering the digestive system of the ruminant. The ECE generally acts to improve the natural digestion of structural carbohydrates and can include any such enzyme naturally secreted in the digestive tract of the ruminant or otherwise required to digest structural carbohydrates found in the forage that is part of the ruminants' diet. In an embodiment of the method, the treated forage is fed to the ruminant prior to activity by ECE on the forage. The ECE may be produced from a carbohydrase enzyme concentrate comprising one class of carbohydrase enzyme or a plurality of classes of carbohydrase enzymes. In an embodiment of the method, the ECE may comprise cellulase, cellobiase, arabanase, pectanase, polygalacturonase, xylanase class of carbohydrase enzymes, or any combinations thereof. In an embodiment, the ECE comprises one or more purified enzymes.

In an embodiment, the ECE concentrate is diluted to form an aqueous ECE solution. The aqueous ECE solution may be applied by spraying or otherwise spreading onto the forage. In an embodiment, the aqueous ECE solution may be sprayed in a solid cone pattern onto the forage at a rate of from 10-60 gallons per minute for about 3-30 minutes. In another embodiment, the aqueous ECE solution may be sprayed in a solid cone pattern onto the forage at a rate of about 10-60 gallons per minute for approximately 3-5 minute. In other embodiments, the ECE is provided in a dry form, such as a powder or fine granules, and is spread over or otherwise added to the forage. In some instances, the forage may be additionally mixed or turned to ensure more even distribution of the added ECE throughout the forage and/or across the forage particle surface area. The mixing may occur during the addition of the ECE, after the addition of the ECE, or both. The mixing or turning may be performed mechanically by known methods, such as using an auger.

Alkali

The addition of alkali to a forage with a low level of ammonia acts to increase the access to enzyme binding sites on the polysaccharides of the forage material to improve ECE effectiveness. If the level of ammonia in a forage is 0.0-1.4% of dry matter (crude protein equivalent/% dry matter), then alkali is applied to the forage at a dosage of 0.25% to 0.75% of dry matter (wt/wt) prior to application of the ECE. If the level of ammonia in the forage is greater than 1.4% of dry matter (crude protein equivalent/% dry matter), then no alkali is applied before application of ECE. In an embodiment, the alkali may be sodium hydroxide (NaOH), potassium hydroxide (KOH) or any other suitable water soluble alkali known in the art. In another embodiment, an alkali that is approved by AAFCO (American Association of Feed Control Officials) may be used, such as sodium hydroxide, potassium hydroxide, calcium hydroxide (CaOH) or magnesium hydroxide (MgOH).

Similar to the ECE preparation previously described, the alkali may be diluted with water to form an aqueous alkali solution that is sprayed or otherwise spread onto the forage. In an embodiment the aqueous alkali solution may be sprayed in a solid cone pattern onto the forage at a rate of from 10-80 gallons or 80-640 lbs. of solution per minute for about 3-30 minutes. In another embodiment, the aqueous alkali solution may be sprayed in a solid cone pattern onto the forage at a rate of from 10-80 gallons or 80-640 lbs. of solution per minute for about 3-5 minutes. In an embodiment, the alkali is diluted to the desired dosage in 2000-10,000 ml of water. Suitable spray nozzles may be used that comprise an orifice that is sized from about 0.05 to 0.20 inches and a typical installation would have from two to six such spray nozzles. The orifice size and number of spray nozzles selected depend on the rate of application required and the quantity of forage to be treated. Such methods of application are suitable for treating commercial quantities of forage, for example about 500-50,000 lbs. of forage, however it is envisioned that one or more of the disclosed methods may be scaled for smaller quantities of forage.

The alkali may be diluted using methods known in the art to form an aqueous solution of the alkali (hydroxide solubilities are well known in the art, e.g., NaOH=1,100 WI at 25° C., KOH=1,210 g/l at 25° C., CaOH=1.7 g/l at 20° C., and MgOH=0.006 WI at 25° C.). In other embodiments, the alkali is provided in a dry form, such as a powder or fine granules, and is spread over or otherwise added to the forage. In some instances, the forage may be additionally mixed or turned to ensure more even distribution of the added alkali throughout the forage and/or across the forage particle surface area. The mixing may occur during the addition of the alkali, after the addition of the alkali, or both. The mixing or turning may be performed mechanically by known methods, such as using an auger. In an embodiment, the alkali is applied at least 0.10% but no more than 0.99% (wt/wt) of forage dry matter.

Embodiments of the disclosed method may employ at least one of the alkali and ECE being in solution. Another embodiment of the disclosed method may employ at least one of the alkali or ECE being in a dry form. In an embodiment, at least 20-200 ml of an aqueous alkali or ECE solution is applied at a desired concentration per pound of forage dry matter. With the relatively high volumes of dilute solution per pound (i.e. ≥200 ml per pound) adequate dispersion can be obtained by spraying the aqueous alkali (or ECE) solution over the feed load at a rate of approximately 10-40 gallons per minute while turning and mixing for a relatively short time, approximately 3 to 5 minutes. In another embodiment, a relatively low volume of aqueous alkali or ECE solution is applied per pound of forage dry matter (e.g., 20 ml of aqueous ECE solution per pound of forage), but with an increased application time. That is, for lower volumes of aqueous alkali or ECE solutions, an application rate of approximately 0.5 to 2 gallons per minute is employed with an application time on the order of approximately 10 minutes in order to achieve adequate dispersion of alkali or ECE. Generally, as the solution volume per pound of forage dry matter decreases, the length of application time increases to ensure that alkali or ECE is evenly distributed throughout the forage.

The aqueous alkali solution and the aqueous ECE solution can be applied to fibrous materials, such as forage, immediately before ingestion by a ruminant. Preferably, the forage is mechanically turned and mixed as the aqueous alkali and ECE solutions are applied, for example by a reel or an auger, to ensure uniform coverage. In some applications, it may be desirable to heat the fibrous material prior to application of the ECE. Alternatively, the aqueous ECE solution can be heated to a maximum temperature of about 140° F. for application. This maximum application temperature is selected to prevent degradation or denaturation of the ECE.

The methods disclosed herein increase rate and extent of fiber digestion by ruminants. The disclosed methods may be practiced over a range of temperatures and at ambient or atmospheric pressure. In fact, it is believed the dilute aqueous ECE solution may be applied from approximately a freezing temperature to 140° F. The upper temperature limit is substantially determined by the denaturing temperatures of the enzymes. The disclosed methods of treating forage were observed to increase the rate and extent of fiber digestion without requiring compression of the forage. Once coverage of the forage with the treatments (alkali and/or ECE) is achieved, it is not necessary to subject the wetted forage to subsequent mechanical compacting pressure or compression before feeding to the ruminant. Mechanical turning and mixing and uniformly applying an effective amount of the alkali and or ECE over the surface of the forage may be done with an auger while applying the aqueous alkali and ECE solutions over the surface by spraying.

The following examples are offered by way of illustration and not by way of limitation.

Example 1

One of the factors affecting the efficacy of the ECE when applied directly to plant materials is the ability of the ECE to bind to active sites within the structure of the plant. Cutin is an insoluble material composed of palmitic and oleic fatty acids and glycerol, which acts as a barrier to pathogens, and also controls water loss and permeability to gases. To make the ECE more effective, the cutin barrier needs to be at least partially saponified. This example demonstrates that saponification can be achieved by treatment with a mild alkali. Saponification provides increased access to the necessary ECE binding sites, which allows for improved NDFd at low concentrations of alkali. Current alkali treatments that are employed use a much higher concentrations of alkali, relying instead on the alkali reaction to degrade the ester and ether linkages among the hemicellulose and lignin structure. This example also demonstrates a method that improves corn silage NDFd, thereby improving dairy productivity. The treatment of forage and feeding of cows in a typical dairy farming application was simulated in-vitro. For silages with ammonia levels of 1.4% and below, if alkali pretreatment was applied at dosages of 0.25-0.75% wt/wt (i.e., at 0.25%, 0.50/o and 0.75% wt/wt), a statistically significant improvement in NDFd was observed.

In this example, fresh corn silage samples were collected from twenty (20) different dairies spanning four (4) crop years from 2014 to 2017. The samples collected represented agronomic growing conditions from across the U.S. milk producing areas ranging from non-irrigated temperate climates to irrigated arid climates. The fresh samples of corn silage were collected from cooperating dairies, sub-divided, and vacuum sealed in air tight bags. The samples represented both conventional and brown mid-rib genetic varieties, grown under non-irrigated, temperate and irrigated, desert agronomic conditions, and across multiple cropping seasons. After being sub-divided and vacuum sealed, one sub-sample was shipped overnight to a laboratory and analyzed upon arrival for dry matter and ammonia content. The amount of dry matter in the sample was determined in a two-step procedure. The first step was partial drying of the sample using known methods (For example, the method used in Goering, H. K., P. J. VanSoest, 1970. Forage Fiber Analysis-Apparatus, Reagents, Procedures, and Some Applications. ARS/USDA Handbook No. 379, Superintendent of Documents, U.S. Government Printing Office, Washington, DC, USA). The second step was drying of the sample in a forced air oven at 105° C. for (3) three hours per National Forage Testing Association recommendations.

The ammonia content was determined by placing 25 grams of as-received forage sample in 200 ml of deionized water. Samples were left overnight, then were blended for (2) two minutes and filtered through 20-25 micron filter paper. The filtrate was collected and 25 ml of the collected filtrate was mixed with 75 ml of deionized water and introduced to a Labconco Rapidstill II analyzer. The sample was then titrated with 0.1N hydrochloric acid (HCl) to determine ammonia level. The remaining sub-samples were shipped overnight to the Department of Animal Science, Cornell University, Ithaca, NY and stored at 7° C. until processed and analyzed. The samples were removed from storage and processed in a commercial food processor (Robot Coupe, Model R2 NCLR5) to reduce the particle size and to create a uniform particle size, which was approximately 1 mm wide×3 mm long×0.2 mm thick to 7 mm wide×20 mm long×4 mm thick (thereby producing a size that can be used in the 125 ml Erlenmeyer flask so that the material stays in the buffer and rumen fluid medium). Processing the as-received samples with a food processor, as described above, was the only alteration made to the as-received samples.

The NDFd was determined after in-vitro incubation (30-hour NDFd) in rumen fluid using the procedure described in H. K. Goering (Goering, H. K., P. J. VanSoest. 1970. Forage Fiber Analysis—Apparatus, Reagents, Procedures, and Some Applications. ARS/USDA Handbook No. 379, Superintendent of Documents, U.S. Government Printing Office, Washington, DC, USA) using NDF as the fiber measurement, which is known in the art. All samples were analyzed in duplicate and fermentation controls (a corn silage standard used in all analyses) were also analyzed to ensure uniformity among and within treatment periods. The ECE used was a commercial proprietary blend of carbohydrase enzymes that is active on an NDF matrix. The ECE used included Cellulase 11,500 ECU/ml (ECU=endo-cellulase unit); Xylanase 28,750 BXU/ml (BXU=beta-xylanase unit); Polygalacturonase 45.5 PGU/ml (PGU=endo-polygalacturonase unit).

The ECE liquid concentrate was diluted at a ratio of 468 µl of concentrate in 100 ml of water. After particle size reduction with the food processor, the silage material was spread out on flat surface covered with plastic and the dilute aqueous ECE solution was sprayed onto the forage using a Sure Shot Milwaukee Sprayer with a maximum capacity of 24 oz. The forage was stirred, turned, and mixed while the solution was being applied to insure adequate coverage of the particle surface area. The dilute aqueous ECE solution was applied at rate of 350 ml/kg. The dilute aqueous ECE solutions in these trials were applied two hours prior to in-vitro incubation in the flasks (i.e., 2 hours prior to feeding to a ruminant).

The alkali treatments were prepared the day before application to the forage, and allowed to normalize. Six different aqueous alkali solutions were prepared ranging from a 0.181M solution to a 3.571M solution. All solutions were applied at rate of 350 ml/kg dry matter forage. The specific alkali solutions are listed in Table 1 below.

TABLE 1

| NaOH as % Dry Matter Forage (wt/wt) | NaOH (gm/kg Dry Matter Forage) | NaOH (mole/kg Dry Matter) | Molar (M) Solution | Application Rate (ml/kg Forage Dry Matter) |
|---|---|---|---|---|
| 0.25% | 2.5 | 0.063 | 0.181 | 350 |
| 0.50% | 5.0 | 0.125 | 0.357 | 350 |
| 1.00% | 10.0 | 0.250 | 0.714 | 350 |
| 2.00% | 20.0 | 0.500 | 1.429 | 350 |
| 2.50% | 25.0 | 0.625 | 1.786 | 350 |
| 5.00% | 50.0 | 1.250 | 3.571 | 350 |

The alkali pre-treatments were applied using a Sure Shot Milwaukee Sprayer. Silage material was spread out on flat surface covered with plastic, stirred, turned, and mixed while the dilute aqueous alkali solution was being applied to insure adequate coverage particle surface area. The alkali pre-treatments were applied separately from and immediately prior to the ECE treatment.

The results of the experiments were analyzed using SAS software, which is a standard software for statistical analysis in science and medicine. The statistical model used was a generalized linear model. Factors evaluated were forage source, ammonia content of the forages, and the treatment used (Control, ECE, NaOH, or ECE+NaOH). Least square means were calculated and a Tukey's adjustment was added to evaluate treatment ammonia content comparisons. The Tukey's adjustment allows for comparisons of all treatment means for hypothesis testing and provides confidence intervals. The normality of the data was evaluated using the Proc Univariate procedure of SAS to ensure there was no bias in the treatment outcomes due to some unusual forage type or sample. Significance was declared at $P<0.05$, meaning any comparison made to the control that achieved that level of probability was not due to random chance and the hypothesis was accepted.

Results of statistical analysis of the in-vitro data across all samples is presented in Table 2 below and shows that the application of an exogenous carbohydrase enzyme (ECE) cocktail alone to corn silage had a minor (2.8%), non-statistically significant (NS), improvement in NDFd as compared to control samples treated with water alone.

TABLE 2

|  | 30 hr NDFd | | |
| --- | --- | --- | --- |
|  | CONTROL (%) | ECE (%) | Δ | p= |
| All Samples | 46.2 | 47.5 | +2.8% | NS |

A sub-set of corn silages within the total sample set in this example were designated as containing high ammonia levels. Any silage with an ammonia ($NH_3$) level at or above 1.4% (crude protein equivalent/% dry matter) of dry matter was classified as being a HIGH $NH_3$ corn silage. Any silage with an ammonia level below 1.4% (crude protein equivalent/% dry matter) of dry matter was classified as being a LOW $NH_3$ corn silage. Both HIGH and LOW $NH_3$ silages were treated with water alone and NDFd results were determined and are shown in Table 3. Statistical analysis of the results indicated that any difference observed was not statistically significant (NS).

TABLE 3

| 30 hr NDFd | | | |
| --- | --- | --- | --- |
| LOW $NH_3$ (%) | HIGH $NH_3$ (%) | Δ | p= |
| 46.6 | 44.2 | −5.2% | NS |

Table 4 compares the NDFd in HIGH $NH_3$ and LOW $NH_3$ corn silages treated with water alone (control) with the NDFd in HIGH $NH_3$ and LOW $NH_3$ corn silages treated with an ECE alone. Application of an ECE to LOW $NH_3$ corn silages was found to have no statistically significant (NS) impact on the NDFd. However, application of an ECE to HIGH $NH_3$ corn silages resulted in a 20% improvement in NDFd (44.2 vs 53.2).

TABLE 4

|  | 30 hr NDFd | | |
| --- | --- | --- | --- |
|  | CONTROL (%) | ECE (%) | Δ | P= |
| LOW $NH_3$ | 46.6 | 46.8 | 0.0% | NS |
| HIGH $NH_3$ | 44.2 | 53.2 | +20.0% | <0.01 |

The results of NDFd with the addition of an aqueous alkali were statistically analyzed and are shown in Table 5 below. A control batch of forage was treated with water only and other batches of forage were treated with alkali. The alkali used was an aqueous sodium hydroxide (NaOH) solution and the alkali dosage was titrated from 0.25% to 5.00% wt/wt of forage dry matter. When aqueous NaOH solution was applied alone at a dosage of 5.00% of forage dry matter (wt/wt), there was an 18.8% (54.2% vs 45.6%) improvement in NDFd (which was statistically significant). In contrast, the application of aqueous NaOH solution alone at dosages less than 5.0% of forage dry matter (wt/wt) had no statistically significant (NS) effect on NDFd.

TABLE 5

|  | 30 hr NDFd (%) | Δ | p= |
| --- | --- | --- | --- |
| CONTROL | 45.6 | — | — |
| 0.25% NaOH (wt/wt) | 41.3 | −9.4% | NS |
| 0.50% NaOH (wt/wt) | 49.0 | +7.5% | NS |
| 1.00% NaOH (wt/wt) | 44.4 | −2.6% | NS |
| 2.00% NaOH (wt/wt) | 49.4 | +8.3% | NS |
| 5.00% NaOH (wt/wt) | 54.2 | +18.8% | 0.02 |

When titrated dosages of aqueous NaOH solutions were used as a pre-treatment before the application of ECE, statistical analysis showed a linear negative correlation between NaOH dosage level and NDFd improvement. Pre-treating the forage with aqueous dilutions of NaOH at the dosages of 0.25%, 0.50%, and 0.75% of dry matter (wt/wt) prior to treatment with ECE resulted in a statistically significant improvement in NDFd as is shown in Table 6. Both the high magnitude of the response and the statistical significance of the response were surprising and unexpected. By contrast, there was no statistically significant (NS) improvement in the NDFd when aqueous dilutions of NaOH were applied as pre-treatments at a dosage of 1.00% of dry matter (wt/wt). A control batch of forage was treated only with water.

TABLE 6

|  | 30 hr NDFd (%) | Δ | p= |
| --- | --- | --- | --- |
| CONTROL | 46.0 |  |  |
| NaOH + ECE | 47.1 | +2.4% | NS |
| 0.25% NaOH (wt/wt) + ECE | 57.3 | +24.6% | <0.01 |
| 0.50% NaOH (wt/wt) + ECE | 53.0 | +15.2% | <0.01 |
| 0.75% NaOH (wt/wt) + ECE | 54.7 | +18.9% | 0.02 |
| 1.00% NaOH (wt/wt) + ECE | 50.7 | +10.2% | NS |

In summary, Table 2 shows that application of an exogenous carbohydrase enzyme (ECE) cocktail alone to corn silage resulted in a minor, 2.8%, non-statistically significant improvement in NDFd compared to control samples treated with water alone. Table 4 shows that application of ECE alone to silages with ammonia levels above 1.4% resulted in a 20% improvement in NDFd, which was statistically significant. For silages with ammonia levels at 1.4% and below, if alkali pretreatment was at 0.25-0.75%, (i.e., at 0.25%, 0.50% and 0.75%) statistically significant improvements in NDFd of 24.6%, 15.2%, and 18.9%, respectively, were observed.

This example demonstrates that saponification of the cutin can be achieved through mild alkali treatment. Saponification provides increased access to the necessary ECE binding sites, which allows for improved NDFd. This example also demonstrates a method that improves corn silage NDFd, thereby improving dairy productivity. For silages with ammonia levels of 1.4% (crude protein equivalent/% dry matter) and below, if alkali pretreatment was applied at dosages of 0.25-0.75% wt/wt (i.e., at 0.25%, 0.50% and 0.75% wt/wt), then statistically significant improvements in NDFd were observed.

Example 2

An in-vivo lactation trial was conducted to validate the in-vitro findings observed in Example 1. Two pens at a commercial dairy were selected to serve as treatment and control pens. Each pen was populated with 180 mature Holstein cows and each pen averaged 180 days (+/−5 days) in milk (or 180 days of lactation) at start of the trial. Pens were designated as Pen #2 and Pen #4. The composition of the standard feed ration for the trial is listed in Table 7 below. This ration was mixed with designated treatment and delivered to the cows once per day. A sample of corn silage was collected and determined to have an ammonia level of 1.12% of dry matter (crude protein equivalent/% dry matter). Given the ammonia level of the corn silage was low (1.4% of dry matter (crude protein equivalent/% dry matter) and below) and corn silage was the primary forage in the standard ration, an alkali pre-treatment was required.

There were three treatment periods in the trial. Treatment period I was a pre-trial period with no alkali pre-treatment or exogenous carbohydrase enzyme (ECE) applied to the standard ration of either pen. In treatment period II, Pen #2 served as the control pen and received the standard ration treated with water only (no alkali pre-treatment or ECE applied). Pen #4 served as the treatment pen and received the standard ration with the alkali and ECE applications.

In treatment period III, the treatment and control pens were switched. Pen #2 served as the treatment pen and received the standard ration with the alkali and ECE treatments applied and Pen #4 served as the control pen and received the standard ration treated with water only. For each treatment period, the cows received the designated treatment for thirty (30) days. At the end of the thirty (30) day period, daily milk weights were collected by cow by a commercial testing lab.

TABLE 7

| | Feed Ingredient | Dry Matter (Pounds per Head per Day) | Dry Matter (Pounds per Load) (180 Head) per Load) |
|---|---|---|---|
| Concentrates | Ground Corn | 12.17 | 2,191 |
| | Canola Meal | 7.56 | 1,361 |
| | Corn Gluten Meal | 0.79 | 142 |
| | By-pass Soybean Meal | 1.96 | 353 |
| | By-pass Fat | 1.25 | 225 |
| | Mineral | 1.43 | 257 |
| | Whey | 1.30 | 234 |
| | TOTAL | 25.16 | 4,763 |
| Forages | Corn Silage | 14.00 | 2,520 |
| | Alfalfa Hay | 6.25 | 1,125 |
| | Oat Silage | 3.00 | 540 |
| | Almond Hulls | 2.26 | 407 |
| | Wet Distillers Grains | 2.14 | 385 |
| | Straw | 1.98 | 356 |
| | TOTAL FORAGE | 29.63 | 5,333 |
| | TOTAL STANDARD RATION | 56.09 | 10,096 |

The alkali pre-treatment was sodium hydroxide (NaOH) applied at a rate of 0.5% of dry matter forage (wt/wt). The NaOH used to make the dilute NaOH treatment was a 50% NaOH solution with a specific gravity of 1.5 gm/ml. Thus, the dosage of 50% NaOH solution was 90 ml per head per day (29.63 lbs. dry matter forage per head per day×0.5% NaOH of forage dry matter/50% NaOH solution×454 gm per lbs./1.5 gm per ml specific gravity=90 ml per head per day).

A commercial ECE concentrate was then applied to the alkali treated forage. The ECE concentrate contained three major classes of enzymes: Cellulase 11,500 ECU/ml (ECU=endo-cellulase unit); Xylanase 28,750 BXU/ml (BXU=beta-xylanase unit); Polygalacturonase 45.5 PGU/ml (PGU=endo-polygalacturonase unit). The ECE was applied at a rate of 0.75 ml per pound of forage dry matter. Thus, the dosage of ECE was 22.0 ml per head per day (29.63 lbs. forage dry matter per head per day×0.75 ml per lbs. forage dry matter=22.0 ml per head per day). Table 8 below shows the composition of aqueous NaOH solution, dilute aqueous ECE solution, and water administered per head per day and per load (180 head of cattle participating in the study).

TABLE 8

| | | Per Head per Day (liters) | | Per Load-180 Head (liters) | |
|---|---|---|---|---|---|
| | | Control | Treatment | Control | Treatment |
| Dilute NaOH Solution | NaOH (50% solution) | 0.000 | 0.090 | 0.00 | 16.20 |
| | Water | 0.000 | 2.410 | 0.00 | 433.80 |
| | TOTAL | 0.000 | 2.500 | 0.00 | 450.00 |
| Dilute ECE Solution | ECE | 0.000 | 0.022 | 0.00 | 4.00 |
| | Water | 0.000 | 2.478 | 0.00 | 446.00 |
| | TOTAL | 0.000 | 2.500 | 0.00 | 450.00 |
| TOTAL Dilute NaOH and Dilute ECE solutions | | 0.000 | 5.000 | 0.00 | 900.00 |
| WATER | | 5.000 | 0.000 | 900.00 | 0.00 |

Table 9 below shows the schedule of dilute aqueous NaOH solution and dilute aqueous ECE solution application per head per day and per load (180 head of cattle participating in the study).

TABLE 9

| | Per Head per Day (lbs.) | | Per Load-180 Head (lbs.) | |
|---|---|---|---|---|
| | Control | Treatment | Control | Treatment |
| Dilute NaOH Solution | 0.00 | 5.50 | 0.00 | 990.00 |
| Dilute ECE Solution | 0.00 | 5.50 | 0.00 | 990.00 |
| TOTAL NaOH and ECE solutions | 0.00 | 11.00 | 0.00 | 1,980.00 |
| WATER | 11.00 | 0.00 | 1,980.00 | 0.00 |

To prepare the feed rations, all ingredients listed in Table 7 were weighed into a vertical mixer fitted with a digital scale. The mixer was then positioned under a spray bar that was configured to apply either the combination of aqueous alkali solution and dilute aqueous ECE solution applied sequentially for the pen receiving the treated feed, or only water for the control pen. The spray bar was fitted with four spray nozzles positioned so the nozzle discharge covered the surface area of the material in mixer. The mixer was operational for the duration of the application of each treatment thereby continually turning and mixing of the feed to provide exposure of all feed particles to the spray bar discharge.

Referring specifically to the feed ration of the treatment pen, the alkali treatment was applied first. The alkali treatment utilized a 50% NaOH solution to make the aqueous NaOH solution. To make and apply the dilute aqueous NaOH solution, a primary water pump configured to deliver 300 lbs. of water per minute to the spray bar was activated. A secondary NaOH pump, which was calibrated to inject 4.91 liter per minute of 50% NaOH into the primary water pump's discharge stream prior to reaching the spray bar, was simultaneously activated. After the desired weight of dilute aqueous NaOH solution (990 lbs.) was added to the mixer, both the primary water pump and the secondary NaOH pump were deactivated. In this example, the application time for the dilute NaOH solution was 3.3 minutes (990 lbs. @300 lbs./minute). During that time, the secondary NaOH pump dispensed the desired 16.20 liters of NaOH per load (4.91 liter per minute×3.3 minutes=16.20 liters). The dilute aqueous ECE solution was applied immediately following application of the dilute alkali solution.

To apply the ECE treatment using the ECE concentrate as the ingredient to make the dilute aqueous ECE solution, the primary water pump configured to deliver 300 lbs. of water per minute to the spray bar was activated. A secondary ECE pump calibrated to inject 1.21 liter per minute of ECE concentrate into the primary water pump's discharge stream prior to reaching the spray bar was simultaneously activated. When the desired weight of dilute aqueous ECE solution (990 lbs.) was added to the mixer, both the primary water pump and the secondary ECE pump were deactivated. In this example, the time of application for the dilute aqueous ECE solution was 3.3 minutes (990 lbs. @300 lbs./minute). The secondary ECE pump accordingly dispensed the desired 4.00 liters of ECE per load (1.21 liter per minute×3.3 minutes=4.00 liters). Once both the dilute NaOH and the dilute aqueous ECE solutions were applied to the standard ration for the treatment pen, the standard ration for the treatment pen was immediately delivered to the cows for ingestion.

For the control pen, only water applied to the forage. The primary water pump was activated delivering 300 lbs. of water per minute to the spray bar. Once the desired weight (1,980 lbs.) of water was added, the primary water pump was deactivated. In this example, the time of application for the water was 6.6 minutes (1,980 lbs. @300 lbs./minute). Once the water was applied to the standard ration for the control pen, the standard ration was immediately delivered to the cows for ingestion.

During treatment period I, daily milk production for Pens #2 and #4 were similar with only a minor difference of 1.4 lbs. (90.1 lbs. vs. 88.7 lbs.). Comparing treatment period I to treatment period II, daily milk production in the control pen (Pen #2) dropped 7.6 lbs. (90.1 lbs. vs. 82.5 lbs.). At the same time daily milk production in the treatment pen (Pen #4) (dilute NaOH solution and dilute ECE solution) gained 24.6 lbs. (88.7 lbs. vs 113.3 lbs.). The pens receiving the dilute NaOH solution and the dilute aqueous ECE solution treatment and the control pens were switched immediately at the end of treatment period II. In treatment period III, daily milk production in the control pen (Pen #4), dropped 13.2 lbs. (113.3 lbs. vs. 110.1 lbs.). At the same time daily milk production in the treatment pen (Pen #2) gained 34.8 lbs. (82.5 lbs. vs 117.3 lbs.). Table 10 below shows milk response to the application of ECE with dilute alkali pre-treatment (lbs. of milk per head per day).

TABLE 10

|  | Treatment Period I (lbs./head/day) | Treatment Period II (lbs./head/day) | Treatment Period III (lbs./head/day) |
| --- | --- | --- | --- |
| Pen #2 | 90.1 | 82.5 | 117.3 |
| Pen #4 | 88.7 | 113.3 | 100.1 |

The in-vivo lactation trial described in this example produced results that validate the in-vitro findings observed in Example 1. Specifically, a positive correlation was observed between NDFd and milk yield in dairy cattle. This indicates that treatment of forage or the feed ration with alkali followed by an ECE treatment results in increased milk yield, thereby improving profitability of milk production.

It should be understood that various changes and modifications to the embodiments described herein will be apparent to those skilled in the art. Such changes and modifications can be made without departing from the spirit and scope of the present disclosure and without diminishing its intended advantages. It is therefore intended that such changes and modifications be covered by the appended claims.

Although several examples have been disclosed in the foregoing specification, it is understood by those skilled in the art that many modifications and other embodiments of the disclosure will come to mind to which the disclosure pertains, having the benefit of the teaching presented in the foregoing description and associated figures. It is thus understood that the disclosure is not limited to the specific embodiments disclosed herein above, and that many modifications and other embodiments are intended to be included within the scope of the appended claims. Moreover, although specific terms are employed herein, as well as in the claim which follows, they are used only in a generic and descriptive sense, and not for the purposes of limiting the present disclosure, nor the claims which follows.

All references cited herein are incorporated herein by reference in their entirety and for all purposes to the same extent as if each individual publication, patent or patent application was specifically and individually indicated to be incorporated by reference in its entirety for all purposes. The citation of any publication is for its disclosure prior to the filing date and should not be construed as an admission that the present invention is not entitled to antedate such publication by virtue of prior invention.

The invention claimed is:

1. A method for increasing fiber digestion of a forage by a ruminant, the method comprising: providing a forage for a ruminant, wherein the forage comprises an ammonia level of 0.0-1.4% of dry matter (crude protein equivalent/% dry matter); administering a treatment to the forage, the treatment comprising, applying an alkali at a dosage of 0.25%-0.75% of dry matter (wt/wt) during a mixing of the forage; applying an aqueous solution of at least one exogenous carbohydrase enzyme during the mixing of the forage, the at least one exogenous carbohydrase enzyme comprising at least 70% active carbohydrase enzyme; and completing the mixing of the forage; and feeding the forage to the ruminant 0-5 minutes after completing the mixing of the forage, wherein the mixing of the forage during the application of the alkali lasts for 3-5 minutes before the applying of the at least one exogenous carbohydrase enzyme, and wherein the mixing of the forage during the application of the at least one exogenous carbohydrase enzyme lasts for 3-5 minutes.

2. The method of claim 1, wherein the alkali comprises one of sodium hydroxide, potassium hydroxide, calcium hydroxide, magnesium hydroxide, sodium carbonate, and potassium carbonate.

3. The method of claim 1, wherein the at least one exogenous carbohydrase enzyme comprises at least one of cellulase, cellobiase, arabanase, pectanase, polygalacturonase, and xylanase.

4. The method of claim 1, wherein the alkali comprises an aqueous solution and is configured to be sprayed onto the forage.

5. The method of claim 4, wherein the aqueous solution comprising the alkali is sprayed in a solid cone pattern at a rate of about 10-60 gallons per minute for about 3-5 minutes.

6. The method of claim 1, wherein the mixing of the forage is done with an auger.

7. The method of claim 1, wherein the increased fiber digestibility leads to a decrease in enteric methane production in at least one of: (1) per liter of milk produced by the ruminant; and (2) per unit of feed consumed by the ruminant, than when the method is not employed.

8. The method of claim 1, wherein each step is performed with the forage maintained at atmospheric pressure.

9. The method of claim 8, wherein the application of the at least one exogenous carbohydrase enzyme is done at a temperature between 32° F. and 140° F.

10. The method of claim 1, wherein the forage comprises at least one of: corn silage; sorghum silage; wheat silage; oat silage; grass silage; and alfalfa silage.

11. A method for treating a forage to increase digestibility by a ruminant, the method comprising:
providing a forage for a ruminant comprising a level of ammonia that is from 0.0% to about 1.4% of dry matter (crude protein equivalent/% dry matter);
applying alkali at a dosage of from about 0.25% to about 0.75% of dry matter (wt/wt) to the forage while mixing for 3-5 minutes;
applying at least one exogenous carbohydrase enzyme to the forage while mixing for an additional 3-5 minutes after the application of the alkali; and
feeding the forage to the ruminant 0-5 minutes after completing the mixing.

12. The method of claim 11, wherein the alkali comprises one of sodium hydroxide, potassium hydroxide, calcium hydroxide, magnesium hydroxide, sodium carbonate, and potassium carbonate.

13. The method of claim 11, wherein the at least one exogenous carbohydrase enzyme comprises at least one of cellulase, cellobiase, arabanase, pectanase, polygalacturonase, and xylanase.

14. The method of claim 11, wherein at least one of the alkali and the at least one exogenous carbohydrase enzyme comprises an aqueous solution.

15. The method of claim 14, wherein the aqueous solution is sprayed onto the forage in a solid cone pattern at a rate of about 10-60 gallons per minute for about 3-5 minutes.

16. The method of claim 11, wherein the at least one exogenous carbohydrase enzyme comprises at least 70% active carbohydrase enzyme.

17. The method of claim 11, wherein the application the at least one exogenous carbohydrase enzyme to the forage is completed about 0-5 minutes before feeding the forage to the ruminant.

18. The method of claim 11, wherein the application of the at least one exogenous carbohydrase enzyme is done while the forage is maintained at a temperature between 32° F. and 140° F.

19. The method of claim 11, wherein the forage comprises at least one of: corn silage; sorghum silage; wheat silage; oat silage; grass silage; and alfalfa silage.

* * * * *